US00PP09888P

United States Patent [19]

Brown et al.

[11] Patent Number: Plant 9,888

[45] Date of Patent: May 6, 1997

[54] CHAMPION DWARF HYBRID BERMUDAGRASS

[76] Inventors: Richard M. Brown, Rte. 4, Box 263; Michael A. Brown, 2611 Del Monte; Scott D. Brown, Rte. 4, Box 230, all of Bay City, Tex. 77414

[21] Appl. No.: 539,122

[22] Filed: Oct. 4, 1995

[51] Int. Cl.[6] ..... A01H 5/00

[52] U.S. Cl. ..... Plt./90

[58] Field of Search ..... Plt./90

[56] References Cited

U.S. PATENT DOCUMENTS

P.P. 9,030 1/1995 Dudeck ..... Plt./90

OTHER PUBLICATIONS

DNA Amplification Fingerprinting Analysis of one Bermudagrass Sample, Plant Molecular Genetics, The University of Tennessee (Jul. 10, 1995).

DNA Amplification Fingerprinting Analysis of one Bermudagrass Sample Report II: Large Range of Primer Test, Plant Molecular Genetics, The University of Tennessee (Aug. 14, 1995).

Beard, James B., "Turf Management for Golf Courses," ©1982 The United States Golf Association, pp. 97, 119, 125.

"Pursuing the Truth," Golf Course Management, Mar. 1994, pp. 5, 7, 108.

Beard, James B., "Recognizing a Lifetime of Achievement," pp. 112, 114, 116, 118, 120.

Beard, James B., "Turfgrass: Science and Culture," ©1973 Prentice-Hall, Inc., pp. 9–12, 138–141.

Caetano-Anollés, G., Callahan, L.M., Williams, P.E., Weaver, K.R., Gresshoff, P.M., "DNA Amplification Fingerprinting Analysis of Bermudagrass (*Cynodon*): Genetic Relationships Between Species and Interspecific Crosses," Theoretical and Applied Genetics.

Vermeulen, P.H., Beard, J.B., Hussey, M.A., and Green, R.L., "Starch Gel Electrophoresis Used for Identification of Turf-type *Cynodon Genotypes*", Reprinted from *Crop Science*, vol. 31, No. 1 (1991), pp. 223–227.

Baker, Jerry, "Jerry Baker's Lawn Book," ©1987 Jerry Baker, pp. 12–13.

"Warm Season Turfgrasses," Turf Management Digest, Farm Press Publications (1992) p. 8.

Trademark Application Ser. No. 74-527,238 for Champion Dwarf Bermuda, filed May 18, 1994.

*Primary Examiner*—James R. Feyrer

*Attorney, Agent, or Firm*—Pravel, Hewitt, Kimball & Krieger

[57] ABSTRACT

A hybrid bermudagrass cultivar, named Champion Dwarf, is distinguished by high rate and density of lateral stem development, low vertical growth characteristic, high density, fine leaf width, and lack of seedhead development. The cultivar is especially suited to golf greens.

11 Drawing Sheets

BACKGROUND OF THE INVENTION

Bermudagrass (Cynodon spp. L. C. Rich) is one of the most important and widely used warm-season turfgrasses. It is adapted to the warm- and subtropic-climatic regions of the world. The turf-type Bermudagrasses are $C_4$, perennials that originated in southeastern Africa. The common turf-type species of Cynodon include: *Cynodon dactylon* (L.) Pers. of *dactylon* Bermudagrass which is a tetraploid; and *Cynodon transvaalensis* (Burtt-Davy) or African Bermudagrass which is a diploid. The *dactylon* Bermudagrasses as a group are characterized by a relatively coarse leaf width and lower shoot density, while the hybrid bermudagrasses tend to have narrower leaf width and higher shoot density. Both are relatively low-growing via vigorous lateral stems, both rhizomes and stolons.

Putting greens in the warm, humid climatic regions of the United States are usually planted with Bermudagrass. There are two Bermudagrass varieties primarily used on putting greens today; Tifgreen (328), released in 1956 and Tifdwarf, released in 1965. Other varieties have been used regionally, but have not gained wide acceptance as the desirable characteristics of Tifgreen and Tifdwarf became more commonly known.

There are six basic components of turfgrass quality: (a) uniformity, (b) density, (c) texture, (d) growth habit, (e) smoothness, and (f) color.

For Bermudagrasses, the primary factor influencing uniformity and smoothness is inflorescence. Most bermudagrasses produce seedheads which rise above the canopy and are generally considered to be unslightly. For use on a putting green, it is desirable to have a variety which has very minimal seedhead formation.

One of the most important components of turfgrass quality is density. Of particular problem for bermudagrass greens is maintaining density at increasingly lower heights. With improvements in equipment and increasing sophistication of golfers, it is now common to find greens regularly mowed at ⅛of an inch. At this height, adequate density becomes critical in order to prevent sunlight from reaching the surface of the soil. When this happens, not only does weed invasion become more of a problem, but given the daily irrigation most greens receive, algae begins to grow on the soil. Algae growing on the putting green further harms the grass, which in turn loses even more density, creating a situation which often leads to thin spots or even bare ground on greens.

In order to accommodate the low mowing heights on a putting green, it is desirable to have a variety which exhibits a fine leaf texture and a vertical leaf orientation. Since greens are usually mowed only once daily, a variety with leaves which do not grow up too quickly would be beneficial in providing a uniform surface for golfers playing several hours after mowing. A variety which possesses rapid lateral growth would be able to more quickly recover from injury due to ball marks, scuffing, and equipment.

Turfgrass species and cultivars selected for putting greens must possess special characteristics including (a) a low, creeping growth habit and erect leaves, (b) tolerance to very close mowing of 0.2 inch (5 millimeters), (c) very high shoot density, (d) fine leaf texture, (e) uniformity, (f) freedom from excessive grain and thatch, and (g) good recuperative rate. Other features are also desirable, such as resistance to pest injury and tolerance to environmental, soil, and traffic stress. A dark-green color does not affect putting quality but does enhance the aesthetics of the course.

SUMMARY OF THE INVENTION

Champion Dwarf is a hybrid bermudagrass (*Cynodon dactylon* ×*Cynodon transvaalensis*) that has the extraordinary morphological characteristics of a very minimal vertical leaf extension rate while at the same time sustaining a dense, rapid lateral stem growth that tolerates extremely close mowing, when compared in replicated studies with the closest known cultivars of Cynodon spp. It also possesses a superior shoot density and a narrower leaf width that makes it an excellent quality surface for putting greens, bowling greens, cricket wickets, croquet courts, and lawn tennis courts. Champion Dwarf is a triploid, hybrid Bermudagrass (*Cynodon dactylon* ×*Cynodon transvaalensis*) with a chromosome number of 2n=27 that has been characterized by replicated DNA amplification fingerprint analysis as being distinctly different compared to the hybrid bermudagrass cultivars, Tifdwarf and Tifgreen.

BRIEF DESCRIPTION OF THE PHOTOGRAPHS

Figure 21:
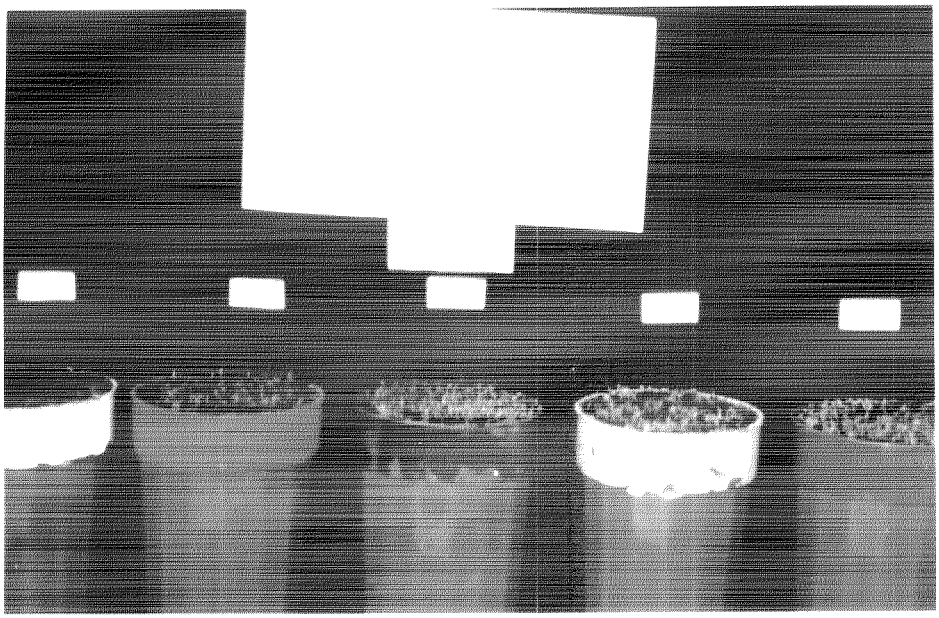
Figure 22:
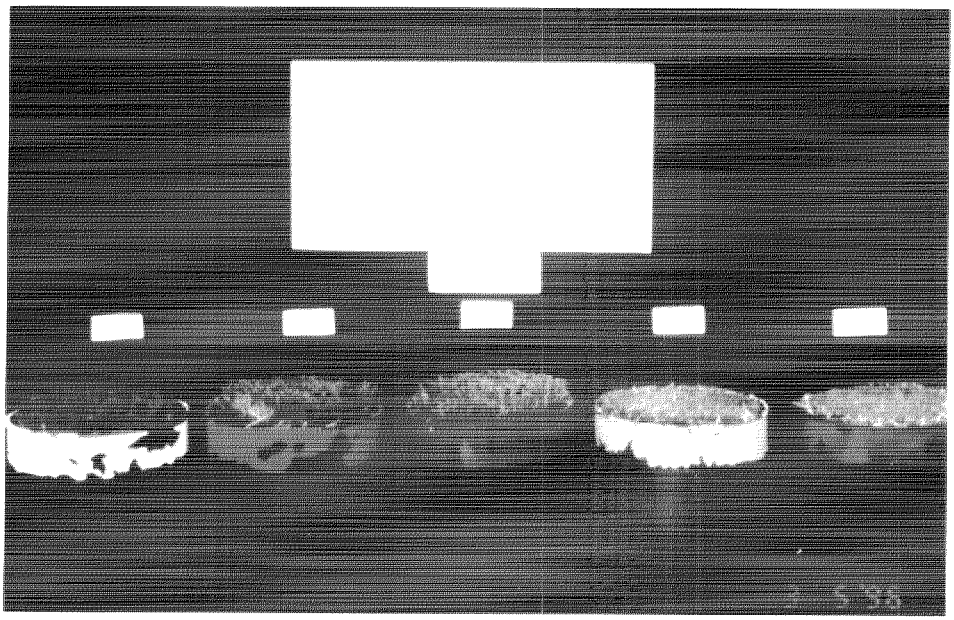

FIG. 21 is a photograph showing pots of Tifdwarf subjected to between 30° and 10° F.; and FIG. 22 is a photograph showing pots of Champion Dwarf subject to between 30° and 10° F.

DETAILED DESCRIPTION OF THE PREFERRED EMBODIMENT

Origin of the Cultivar

The genotype "Champion Dwarf" is a new and distinct natural turfgrass selection from a segregated patch found on a putting green in Walker County, Tex. in 1987. The putting green had been originally planted to Tifdwarf hybrid Bermudagrass (*Cynodon dactylon* ×*Cynodon transvaalensis*) in 1969. The grass was propagated from a single sprig in one-gallon pots at patentees' Bay City, Tex., facility. It was then further cut into individual sprigs and planted in trays, and a 20,000 square feet area was then planted from the trays. This was then propagated into a 1.2 acre growth area. A shorth lateral stem with a single node was used for asexual vegetative propagation and increase of the original source of Champion Dwarf. DNA amplification fingerprint analysis indicates that Champion Dwarf arose either as a somatic mutant out of Tifdwarf hybrid bermudagrass (*Cynodon dactylon* ×*Cynodon transvaalensis*) or from a common ancestor of the two.

Taxonomy —DNA Classification

Figure 1:
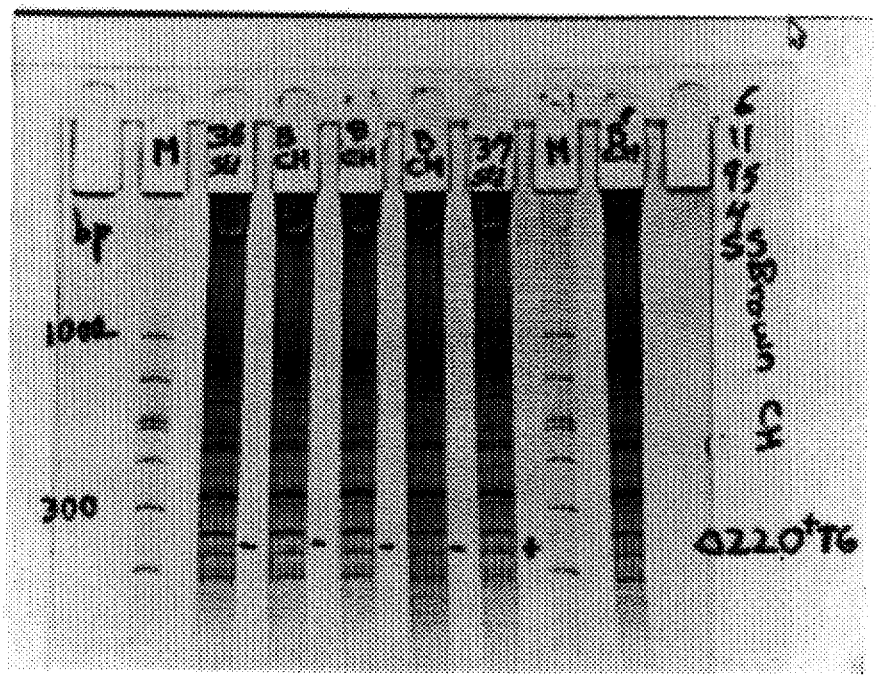
FIG. 1 is a DNA amplification profile comparing bermudagrass cultivars Tifdwarf ("36" in the photograph), Tifgreen ("37" in the photograph), and Champion Dwarf ("B CH" in the photograph)
Figure 2:
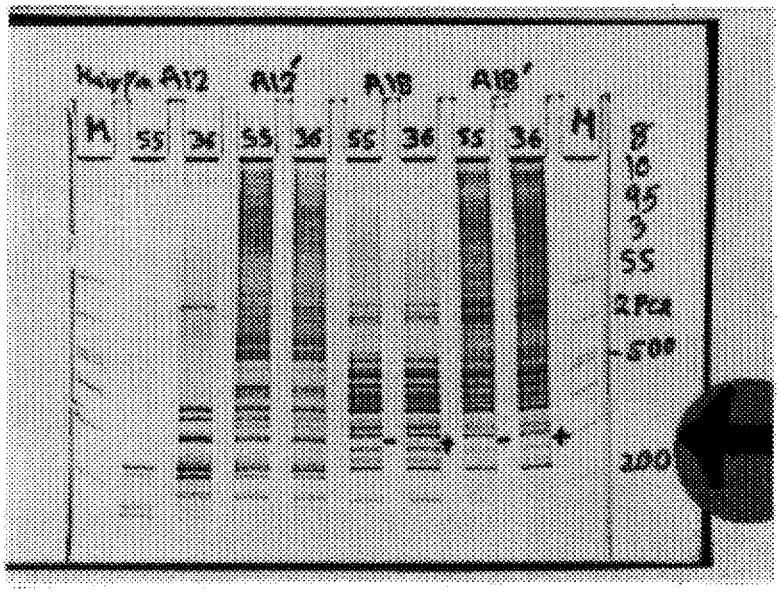
FIGS. 2–5 are DNA amplification profiles comparing Bermudagrass cultivars Tifdwarf ("36" in the photograph) and Champion Dwarf ("SS" in the photograph)
Figure 3:
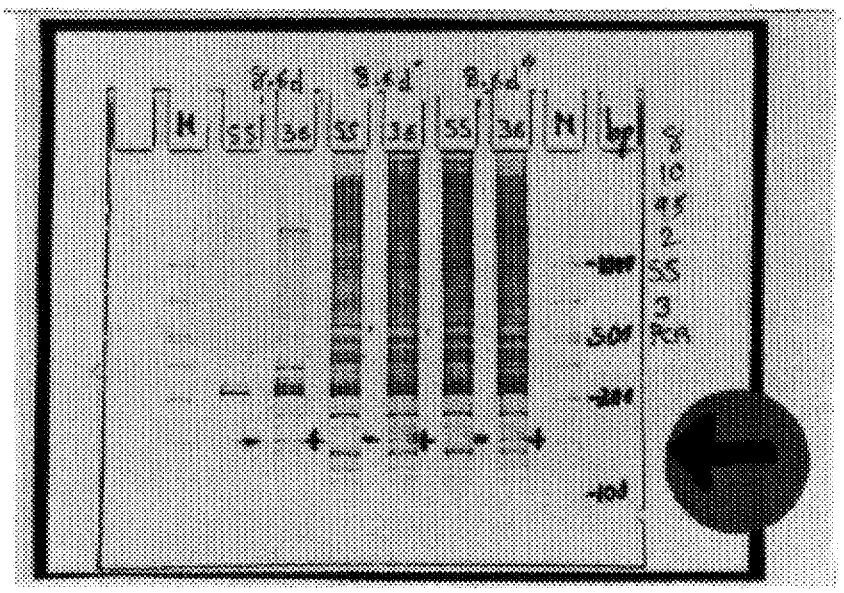
Figure 4:
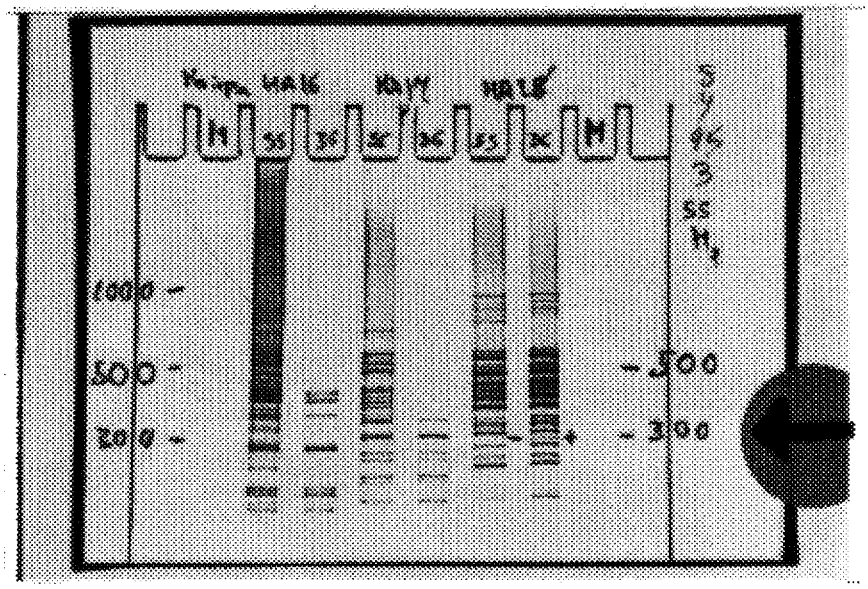
Figure 5:
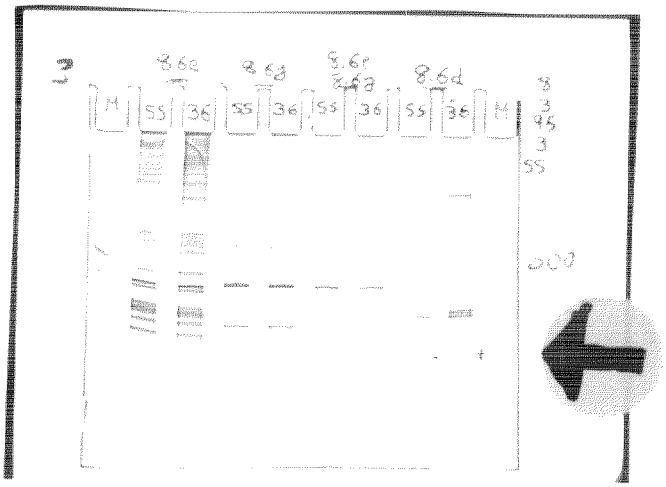

Champion Dwarf is a triploid, hybrid Bermudagrass (*Cynodon dactylon* ×*Cynodon transvaalensis*) with a chromosome number of 2n=27. Characterization by replicated DNA amplification fingerprint analysis has shown Champion Dwarf to be distinctly different from the hybrid Bermudagrass cultivars—Tifdwarf and Tifgreen. FIG. 1 shows a distinctive DNA comparison to Tifgreen. FIGS. 2–5 show distinctive DNA comparisons to Tifdwarf.

Morphological Characterization

Compared to other bermudagrass cultivars, Champion Dwarf has the advantageous morphological characteristics of a very minimal vertical leaf extension rate, while at the same time sustaining a rapid, dense lateral stem growth. It is a very low-growing cultivar with a minimal mowing requirement and improved tolerance to extraordinarily close cutting heights. Furthermore, the rapid speed of lateral stems enables Champion Dwarf to recover rapidly from turf damage, divoting, and ball marks, in comparison to other cultivars. This new and distinct combination of morphological characteristics involving a very slow vertical leaf extension rate and vigorous, dense lateral stem development have been retained through succeeding multiple generations of asexual vegetative propagation. These traits render Champion Dwarf particularly suitable for golf greens and fairways.

Vertical Leaf Extension Rate

Figure 6:
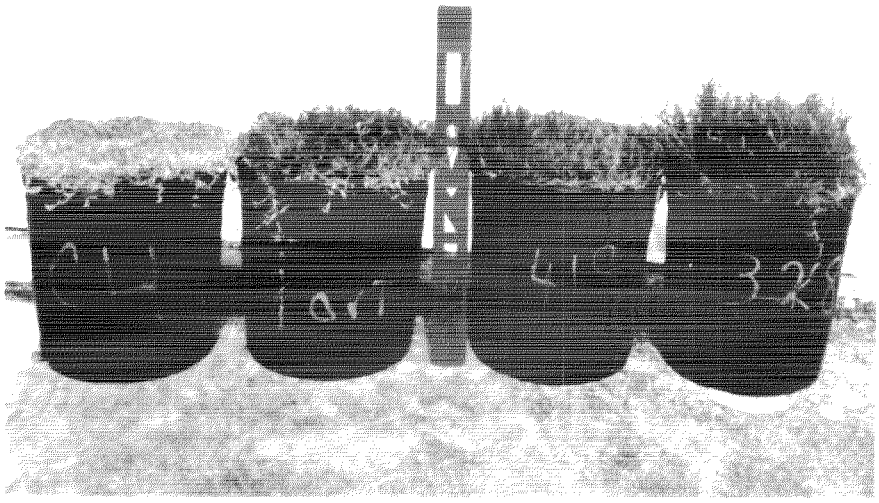
FIG. 6 is a photograph comparing the vertical leaf extension rate of Champion Dwarf to Tifdwarf, Tifway, and Tifgreen after 50 days of growth.

A detailed quantitative assessment of the vertical leaf extension rate under close mowing of 6.4 mm revealed that Champion Dwarf has a significantly slower vertical leaf extension rate, being on the order of 56% slower than Tifdwarf, 73% slower than Tifway, and 82.5% slower than Tifgreen (see Table 1). This characteristic contributes to less resistance to ball roll which translates to a more rapid speed of ball roll on closely-mowed turf surfaces. This is seen in FIG. 6, showing the vertical leaf extension of Champion Dwarf compared to Tifdwarf, Tifgreen, and Tifway after 50 days of growth.

TABLE 1

Vertical Leaf Extension Rate**
Comparisons Among Four Bermudagrass
(Cynodon spp.) Genotypes
ISTI - College Station, Texas - 1995

| Genotype | Vertical Leaf Extension Rate (mm per day) |
|---|---|
| Champion Dwarf | 0.7 a* |
| Tifdwarf | 1.6 b |
| Tifway | 2.6 c |
| Tifgreen | 4.0 d |

*Numbers followed by the same letter(s) are not significantly different based on the Duncan Test (p = 0.05). Total of three replicated growing units.
**Measurements made on 10 leaves per replicate container over 18-day growing period.

Lateral Stem Development

The rates of stolon formation and development were quantitatively assessed based on the number of lateral stems extending outward from the perimeters of replicate containers. Direct comparisons revealed that Champion Dwarf exhibited significantly greater lateral stem development, on the order of 2.6 times that of Tifdwarf, 2.5 times that of Tifway, and 2.8 times that of Tifgreen (see Table 2). This high rate of lateral stem development is the morphological mechanism that contributes substantially to distinctly more rapid rates of turf establishment and turf recovery from damage in comparison to the other three cultivars. FIGS. 7–11 illustrate the comparative stolon production of Champion Dwarf and Tifdwarf, Tifway, and Tifgreen.

TABLE 2

Stolon Number** Comparisons
Among Four Bermudagrass
(Cynodon spp.) Genotypes
ISTI - College Station, Texas - 1995.

| Genotype | Stolon Number (per linear 100 mm) |
|---|---|
| Champion Dwarf | 12.2 a* |
| Tifdwarf | 5.4 b |
| Tifway | 4.8 b |
| Tifgreen | 4.4 b |

*Numbers followed by the same letter(s) are not significantly different based on the Duncan Test (p = 0.05). Total of three replicated growing units.
**Count of the total number of stolons extending outward laterally from the 638 mm perimeter of a replicate container, after 16 days growth.

Turf Recuperative Rate

Quantitative assessments were conducted as to the rate of turf recovery from mechanical injury in which a portion of a mature turf was removed. In comparison to three other hybrid bermudagrass cultivars, Champion Dwarf was found to be significantly superior (see Table 3). It exhibited on the order of 1.8 times more rapid turf recovery rate than Tifgreen, 2.3 times more than Tifway, and 3.4 times more than Tifdwarf. This rapid rate of turf recovery provides a better quality turf surface under intense use, including ball marks, and less proneness to weed invasion.

TABLE 3

Turf Damage Recovery Rate**
Comparisons Among Four Bermudagrass
(Cynodon spp.) Genotypes
ISTI - College Station, Texas - 1995.

| | Turf Recovery Rate (percent) | |
|---|---|---|
| Genotype | Week 3 | Week 4 |
| Champion Dwarf | 68.3 a* | 95.0 a* |
| Tifdwarf | 20.0 c | 76.7 ab |
| Tifgreen | 38.3 b | 65.0 bc |
| Tifway | 30.0 bc | 53.3 c |

*Numbers followed by the same letter(s) in a column are not significantly different based on the Duncan Test (p = 0.05). Total of three replicated growing units.
**Visual estimate of percent turf recovery from a 4 square inch divot-like opening expressed in percent turf recovery per week.

Shoot Density

Figure 7:
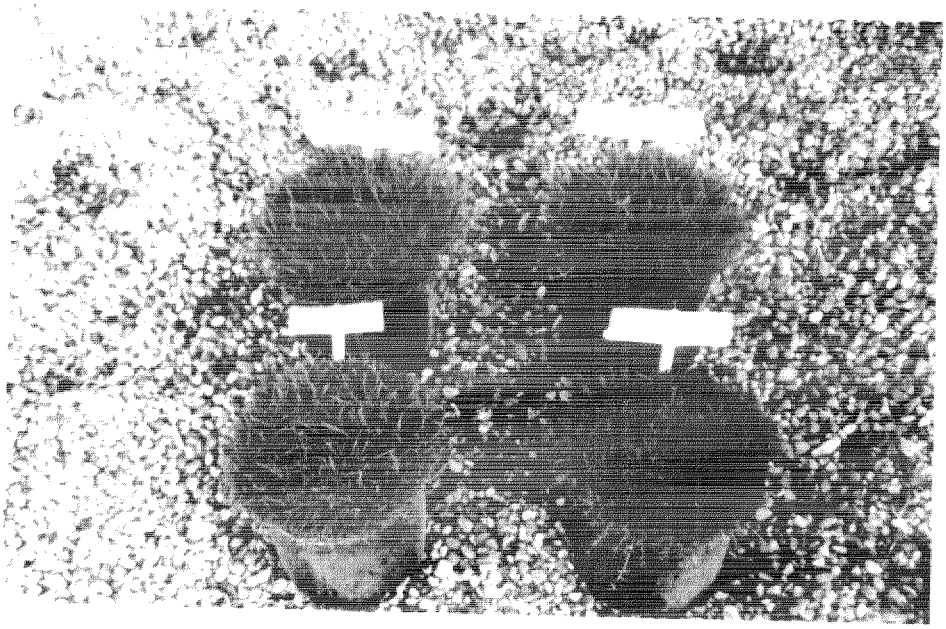
FIG. 7 is a photograph comparing Champion Dwarf with Tifdwarf, Tifway, and Tifgreen showing both lateral stem development and density after 21 days of growth.
Figure 8:
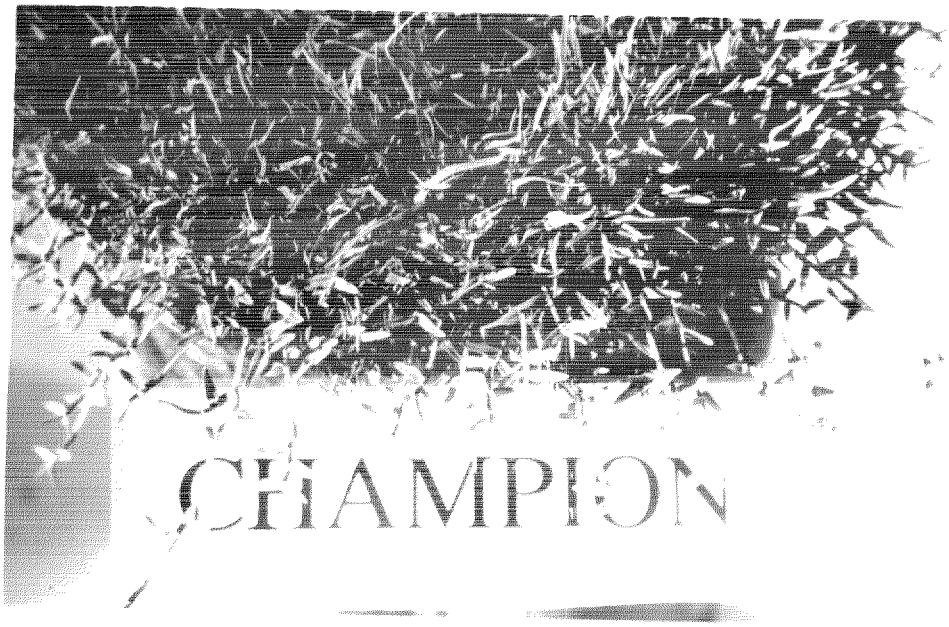
FIGS. 8–11 are photographs comparing Champion Dwarf with Tifway, Tifgreen, and Tifdwarf showing lateral stem development (i.e., stolon production) after 21 days of growth.
Figure 9:
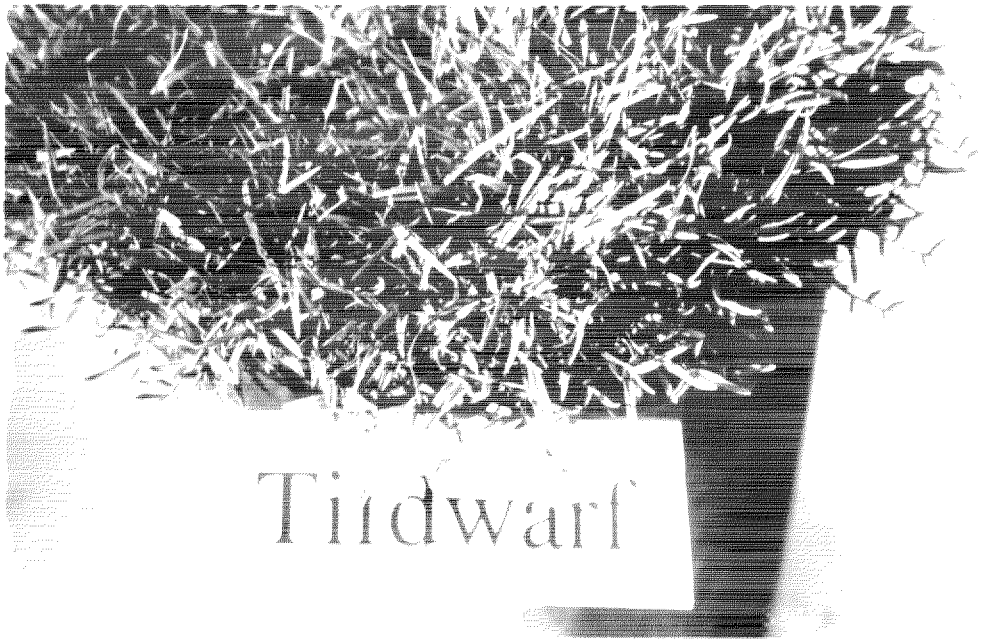
Figure 10:
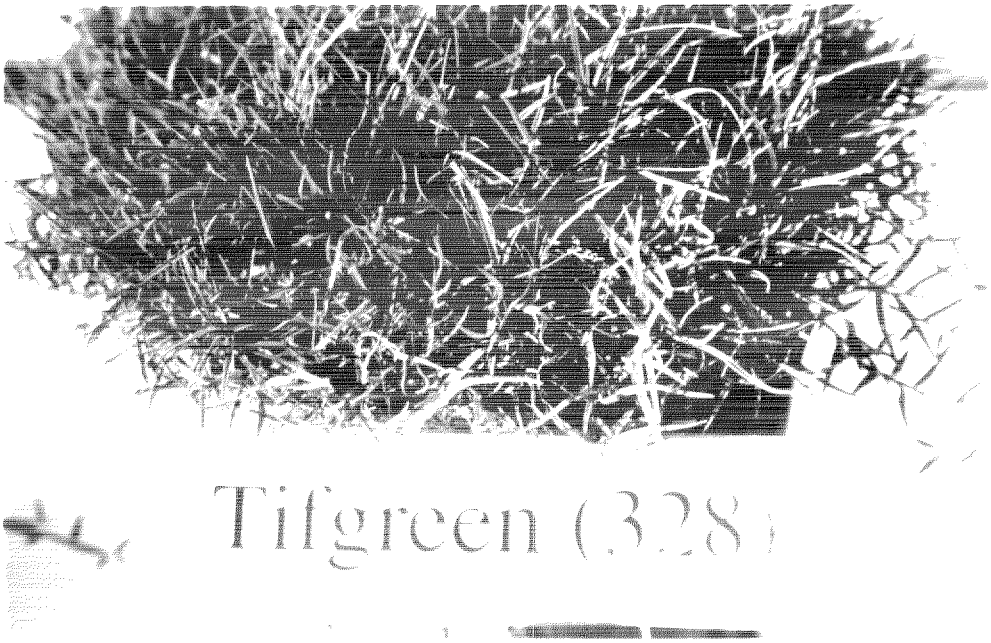
Figure 11:
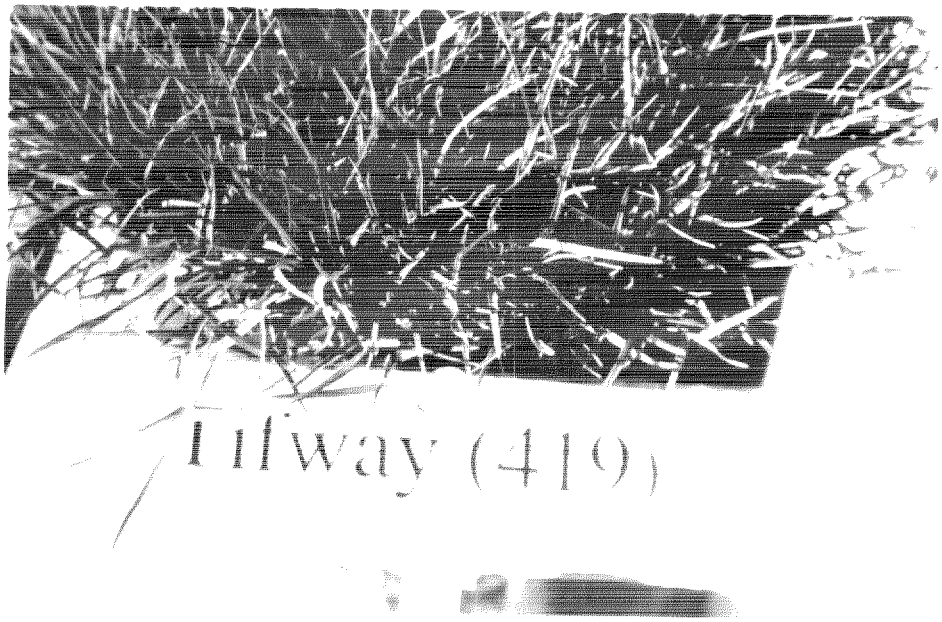
Figure 12:
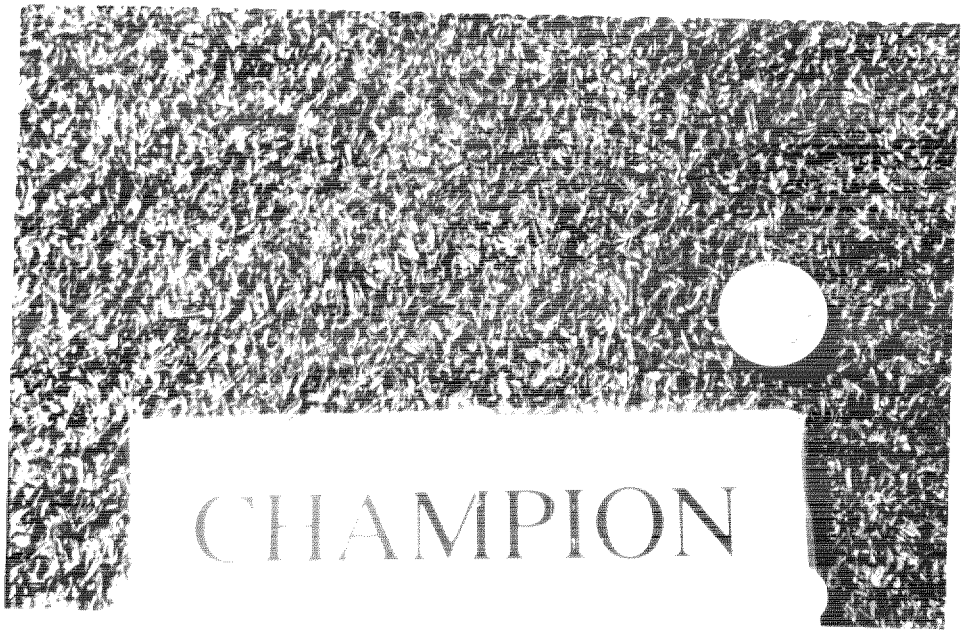
FIGS. 12 and 13 are close-up photographs of Champion Dwarf and Tifdwarf showing densities and leaf widths when mowed to a height of approximately ⅛" inches.
Figure 13:
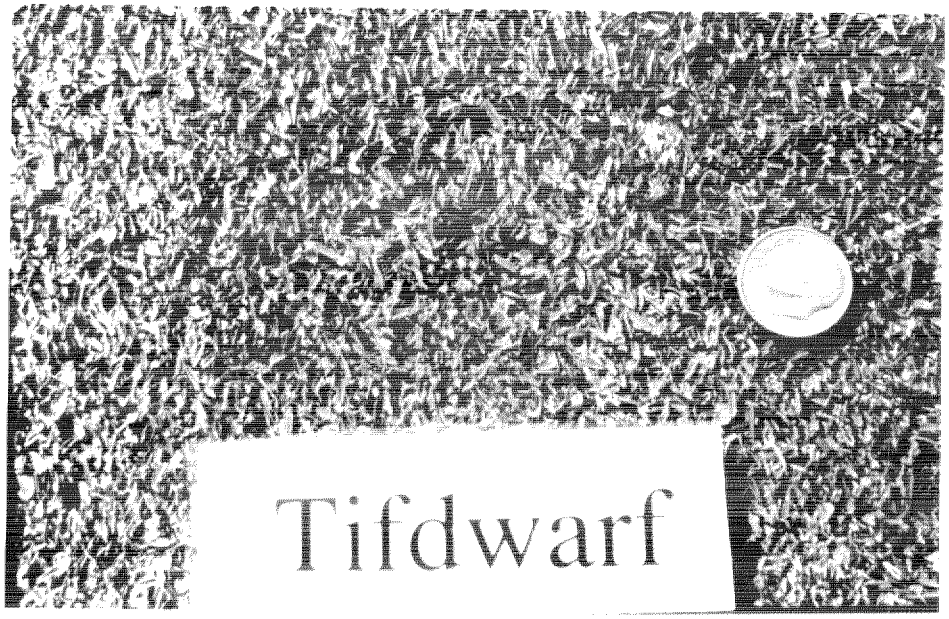

The shoots with leaves originate from nodes along the lateral stems, principally from stolons. A detailed, quantitative assessment was made of the shoot density. Champion Dwarf exhibited a significantly higher shoot density than three hybrid bermudagrass cultivars being on the order of 27.4% greater than Tifdwarf, 66% greater than Tifway, and 118.7% greater than Tifgreen (see Table 4A). FIG. 7 generally shows the comparative density of these grasses, while FIGS. 12 and 13 show the density of Champion Dwarf compared to Tifdwarf. This higher shoot density results in a superior turf surface for closely-mowed putting greens, bowling greens, cricket wickets, croquet courts, and lawn tennis courts.

TABLE 4A

Shoot Density** Comparisons
Among Four Bermudagrass
(Cynodon spp.) Genotypes
ISTI - College Station, Texas - 1995.

| Genotype | Shoot Density (per 100 sq mm) |
|---|---|
| Champion Dwarf | 209.3 a* |
| Tifdwarf | 164.3 b |
| Tifway | 126.1 c |
| Tifgreen | 91.5 c |

*Numbers followed by the same letter(s) are not significantly different based on the Duncan Test (p = 0.05). Total of three replicated growing units.
**Counted on a 64.5 square millimeter (1.0 square inch) area within each replicate container. Counts were taken on mature turfs that had been transplanted onto three replicate containers 77 days earlier. The culture involved close mowing at a 6.4 mm height, plus irrigation.

The internode length and corresponding number of internodes do not vary significantly among the four cultivars. This indicates that the higher shoot density is attributed primarily to a greater number of lateral stems and their vigorous lateral growth in the case of the Champion Dwarf genotype.

A particular concern for Bermudagrass greens is maintaining shoot density at increasingly lower mowing heights. With the improvements in equipment and increasing sophistication of golfers, it is now common to find greens regularly mowed at ⅛". At this height, adequate shoot density becomes critical to prevent sunlight from reaching the surface of the soil. When shoot density is not adequate, weed invasion becomes more of a problem, and given the daily irrigation most greens receive, algae begins to grow in the soil. Champion Dwarf has been found to have a 93% greater density than Tifdwarf Bermudagrass at ⅛" mowing height. This shoot density approaches that of some creeping bent grass cultivars. This is shown by Table 4B below:

TABLE 4B

Shoot Density** Comparisons of Champion and Tifdwarf Bermudagrass Genotypes Under Greens Maintenance

| Cultivar | Shoot Density (per dm sq.) |
|---|---|
| Champion | 2133 a* |
| Tifdwarf | 1104 b |

*Means followed by the same letter in the same column are not significantly different at the 5% LSDt Test.
**Comparative shoot density for Champion and Tifdwarf bermudagrass mowed at ⅛" (3 mm) during the summer and fall. Means of four replications assessed on 11/2/95 at Bay City, Texas.

Formation of Mat

Figure 15:
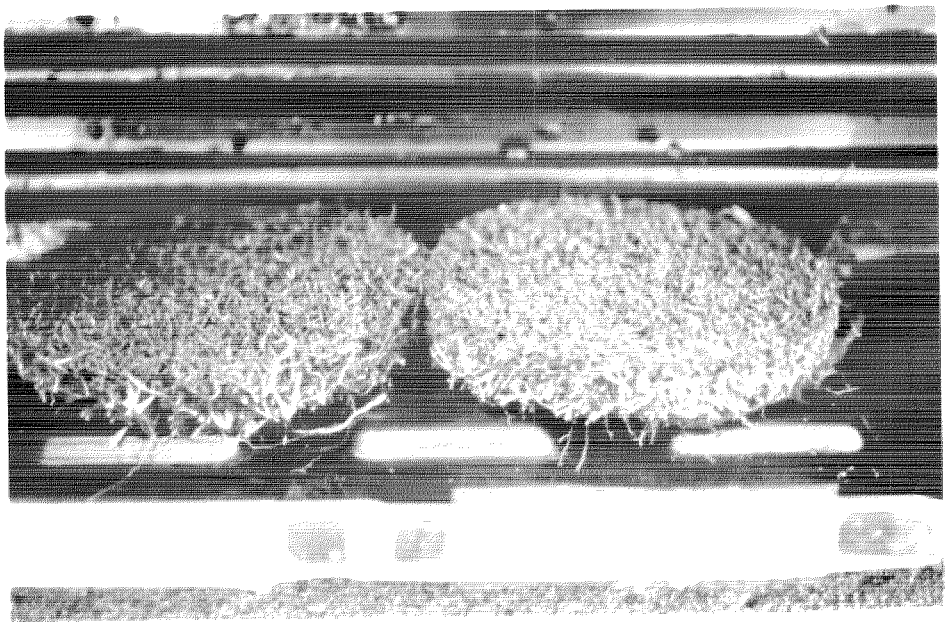
FIGS. 15 and 16 are photographs of side-by-side plugs of Tifdwarf and Champion Dwarf taken from a ⅛" mowed green in October and with the sand washed off to reveal the rhizomes and stolons.
Figure 16:
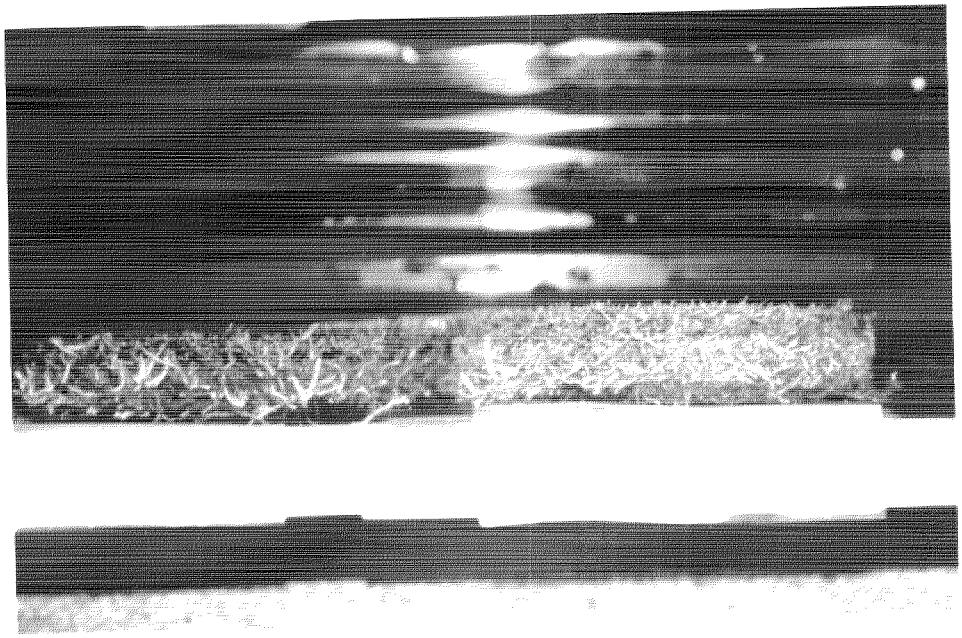
Figure 17:
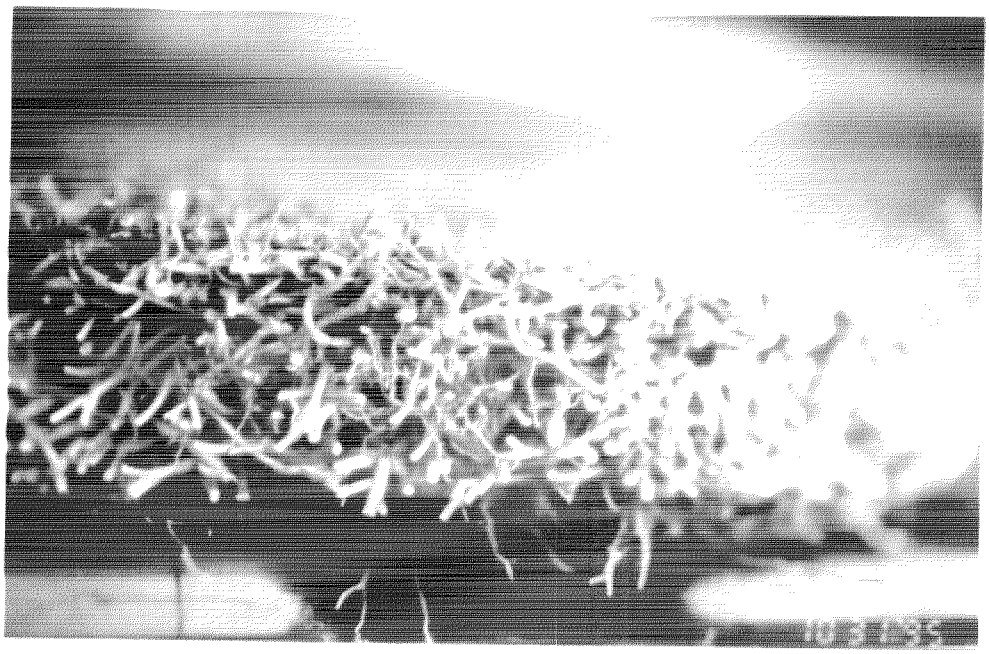
FIG. 17 is a closeup photograph of the plug of Champion Dwarf of FIGS. 15 and 16 revealing the quantities of stolons and rhizomes and depth of the mat and the presence of minimal thatch.

Formation of mat (stolons, rhizomes, sand) just below the surface of the soil is critical to give a green its cushioning effect to withstand traffic from golfers and equipment. A greater number of lateral stems underground also gives the ability to recover more quickly when the surface is damaged. The Champion Dwarf cultivar forms a firm, vigorous mat with nearly three times the depth of Tifdwarf at ⅛" mowing height. This gives Champion Dwarf improved wear tolerance and ability to recover from injury. This is seen in the comparison of the plugs of FIGS. 15 and 16, the close-up side view of a Champion Dwarf plug in FIG. 17, and Table 5. The plugs of FIGS. 15 and 16 were taken from a green with sand washed off to reveal the quantity of rhizomes and stolons of Tifdwarf on the left and Champion Dwarf on the right. The green had been mowed to ⅛" from spring until the photo was taken in October. The side view of FIG. 17 reveals the minimal presence of thatch in the Champion Dwarf plug.

TABLE 5

Formation of Mat** Comparisons of Champion and Tifdwarf Bermudagrass Genotypes under Greens Maintenance

| Cultivar | Depth of Mat (mm) |
|---|---|
| Champion | 15.3 a* |
| Tifdwarf | 5.5 b |

*Means followed by the same letter in the same column are not significantly different at the 5% LSDt Test.
**Comparative depth of mat for Champion and Tifdwarf bermudagrasses mowed at ⅛" (3 mm) during the summer and fall. Means of four replications assessed on 11/19/95 at Bay City, Texas.

Close Mowing Tolerance

Champion Dwarf's very small physical size and superior lateral growth habit give it outstanding tolerance to very close mowing. Very close mowing can mean heights below 5/32". A green in Bay City, Tex., planted with Champion, Tifdwarf, and Tifgreen Bermudagrass was cut at a height of ⅛" from May to mid-December with a 22" Jacobsen walk-behind greens mower with turf-groomer attachment and tournament bedknife.

Mowing of the Tifgreen was discontinued in mid-summer because severe thinning of the stand was occurring due to the close mowing height. Tifdwarf became thin and open by late summer. When rains began in the fall, algae formed where sunlight reached the soil surface.

Champion Dwarf did not show any signs of stress at the ⅛" mowing height, while shoot density continued to improve until reaching 2133 shoots/dm$^2$ which approximates the density of some creeping bentgrass cultivars. Stimp-meter readings were consistently about 9' at this close cutting height.

Champion Dwarf was also cut at 1/10" (100/1,000ths of an inch on an Accu-Gauge) during the months of June and July. Even at this close height, Champion Dwarf suffered no thinning of stand and in fact increased density to 2,537 shoots/dm$^2$. Stimp-meter readings taken during this period exceed 10'. This test demonstrates that Champion Dwarf is capable of withstanding mowing heights as low as the physical limitations of the mowing equipment.

Wear Tolerance

Wear tolerance was tested by imposing a revolving wear simulator which was run for 1900 revolutions and then stopped when there were no leaves remaining on the Tifdwarf shoots. Champion Dwarf demonstrated improved resistance to wear compared to Tifdwarf Bermudagrass on a green mowed at ⅛". This can be partially attributed to the greater density of Champion and a more substantial mat formation below the surface of the soil. This cushion lessens the crushing effect of traffic.

The weight of the shoot biomass (above surface) of Champion Dwarf was 58% greater than the weight of the Tifdwarf shoot biomass before imposition of wear stress, and shoot biomass with Champion was 32% greater by weight than that of Tifdwarf after the imposition of wear stress. A comparative assessment of the Champion Dwarf and Tifdwarf Bermudagrass mowed at ⅛" in the summer and fall is shown below in Table 6.

TABLE 6

Comparative Assessments of Wear Resistance of Champion Dwarf and Tifdwarf Bermudagrass Mowed at ⅛" Summer and Fall

| | Depth of Mat-mm | | Mat Dry wt. per dm sq. | | Shoot Dry wt. per dm sq. | |
|---|---|---|---|---|---|---|
| Cultivar | Non-Wear | Wear | Non-Wear | Wear | Non-Wear | Wear |
| Champion | 15.3 a* | 13.5 a | 137.5 a | 68.1 a | 5.2 a | 1.9 a |
| Tifdwarf | 5.5 b | 5.0 b | 61.2 b | 47.8 b | 2.2 b | 1.3 b |

*Means followed by the same letter in the same column are not significantly different at the 5% LSDt Test.

Resistance to Encroachment

Champion Dwarf has demonstrated superior resistance to encroachment from the Tifway bermudagrass growing on an adjacent collar. This addresses the problem of greens "shrinking" over time due to encroachment from surrounding grasses. A comparison of resistance of Champion Dwarf and Tifdwarf to encroachment is outlined below in Table 7.

TABLE 7

Comparative Assessments of the Resistance to Encroachment into the Champion and Tifdwarf Bermudagrass Greens by the Tifway Bermudagrass Collar Measured from their Common Planting Borders

| Cultivar | Average Length of Encroaching Tifway Stolon (mm) | Number of Tifway Stolons Found in a 15 ft. Linear Section |
|---|---|---|
| Champion | 285 a* | 54 a |
| Tifdwarf | 393 b | 96 b |

*Means followed by the same letter in the same column are not significantly different at the 5% LSDt Test.

Low Temperature Stress Hardiness

Champion Dwarf exhibits greater resistance to low temperature stress than Tifdwarf Bermudagrass. Plugs of Champion Dwarf and Tifdwarf were taken from a sand-based green which had been mowed from May until December at ⅛" and transferred into 30 oz plastic cups. Following dormancy, the cups were placed in a cold chamber for 48 hours at a temperature of 30° F. One replication was then removed and then the temperature was lowered to 25° F. for another 24 hours. Another replication was removed and the temperature was lowered to 20° F. This procedure was continued down to 10° F. Using this procedure, the temperature of the entire soil column from top to bottom was lowered to the ambient temperature within the chamber. This corresponds in the field to a very severe cold temperature stress with the ground being frozen to a depth of over six inches. Results of this study are shown below in Table 8.

TABLE 8

Comparative Low Temperature Stress Resistance Assessments of Champion and Tifdwarf Hybrid Bermudagrass Maintained at a Mowing Height of 3 mm (⅛")

| Recovery Assessment | | Stress Temperature | | | | |
|---|---|---|---|---|---|---|
| Time | Cultivar | 30° F. | 25° F. | 20° F. | 15° F. | 10° F. |
| Week | Champion | 40 a* | 3 c | 0 c | 0 c | 0 c |
| One | Tifdwarf | 33 b | 3 c | 0 c | 0 c | 0 c |
| Week | Champion | 95 a | 95 a | 96 a | 0 c | 0 c |
| Three | Tifdwarf | 60 b | 60 b | 63 b | 0 c | 0 c |
| Week | Champion | 100 a | 98 a | 100 a | 3 c | 0 c |
| Four | Tifdwarf | 80 b | 68 b | 65 b | 0 c | 0 c |
| Week | Champion | 100 a | 100 a | 100 a | 3 c | 0 c |
| Five | Tifdwarf | 83 b | 74 b | 77 b | 0 c | 0 c |

*Means of four replications. Means followed by the same letter in the same row and column are not significantly different at the 5% level LSDt- Test.

Figure 18:
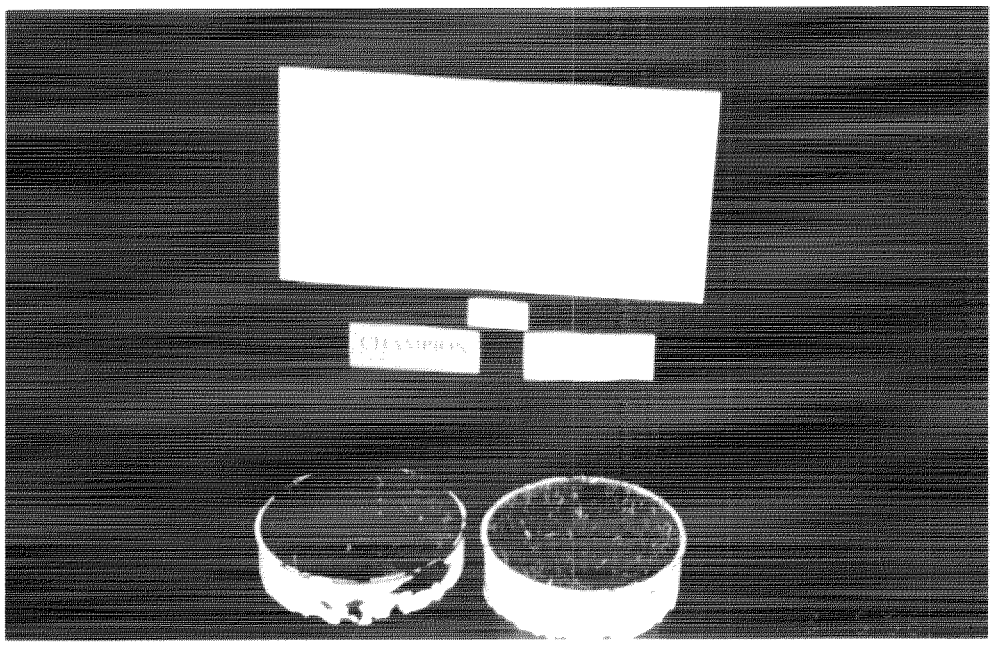
FIGS. 18–20 are side-by-side photographs of pots of Champion Dwarf and Tifdwarf subjected to between 30° and 20° F.
Figure 19:
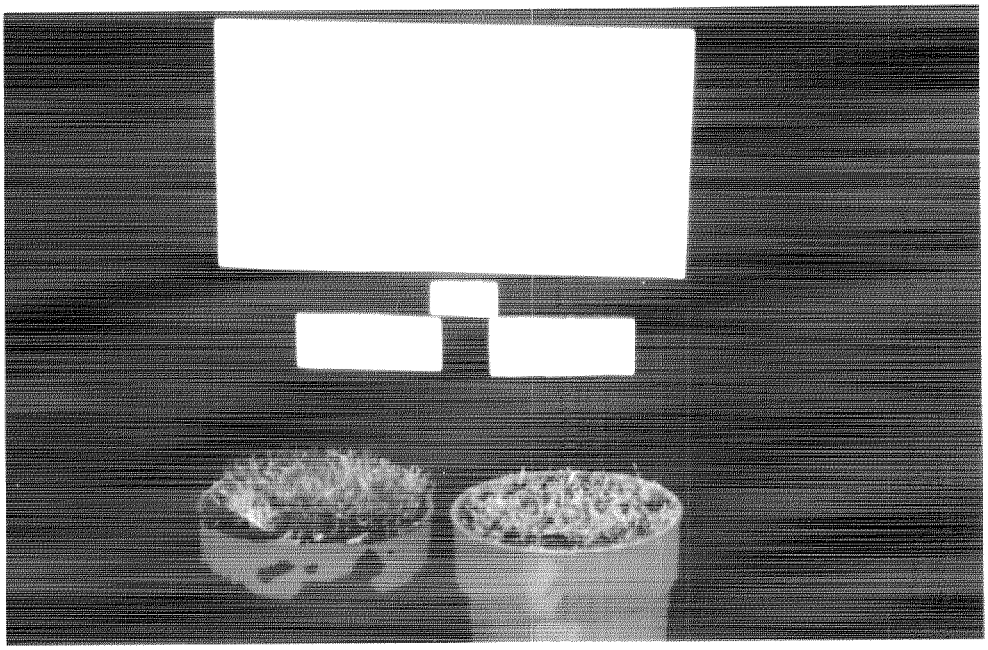
Figure 20:
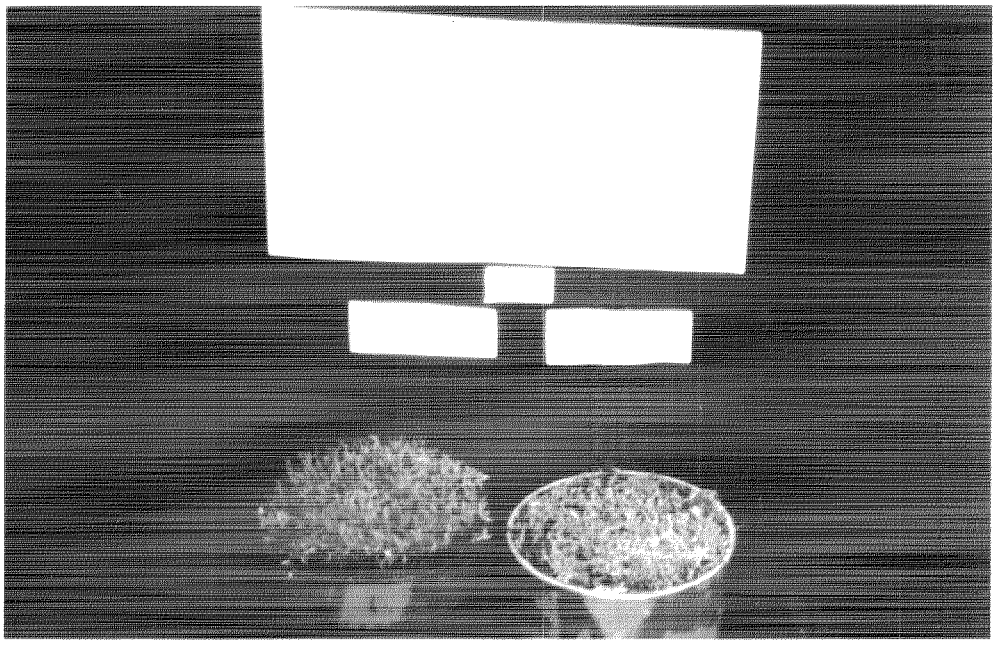

Photographs comparing the two grasses at 30°, 25°, and 20° F. are shown in FIGS. 18–20. A comparison of Tifdwarf to Champion Draft between 30° F. and 10° F. are shown in FIGS. 21 and 22.

Leaf Blade Width

Quantitative assessments of leaf blade widths revealed Champion Dwarf to have a comparatively narrow leaf blade width and allied fine turf canopy texture. The leaf blade width of Champion Dwarf was found to be significantly more fine than three hybrid bermudagrass cultivars, being 13.8% less than Tifdwarf, 23.1% less than Tifway, and 36.3 % less than Tifgreen (see Table 9). The leaf blade width of Champion Dwarf compared to Tifdwarf is seen in FIGS. 12–13.

TABLE 9

Leaf Blade Width** Comparisons Among Four Bermudagrass (Cynodon spp.) Genotypes ISTI - College Station, Texas - 1995.

| Genotype | Leaf Blade Width (mm) |
|---|---|
| Champion Dwarf | 1.00 a* |
| Tifdwarf | 1.16 b |
| Tifway | 1.30 c |
| Tifgreen | 1.57 c |

*Numbers followed by the same letter(s) are not significantly different based on the Duncan Test (p = 0.05). Total of three replicated growing units
**Measured at the midpoint length of the youngest, fully expanded leaf blade on a shoot, with six blade measurements per replicate container.

Inflorescence

In the eight years during which Champion Dwarf has been grown in multiple containers and in multiple field plots in sizes up to 4 acres (1.6 ha), the formation of an inflorescence or seedhead has never been observed on Champion Dwarf under the growing conditions in Texas. This is a unique and distinct characteristic that has not been observed on other commercially available Bermudagrass cultivars.

The observation that Champion Dwarf Bermudagrass does not form seedheads is based not only on the lack of seedheads produced in the Champion cultivar, but also by comparative side-by-side observations with the three other cultivars (Tifway, Tifgreen, and Tifdwarf). Specifically, in side-by-side comparisons, these other cultivars were observed producing seedheads in a glass-house, in field test plots, and in large-acre production field, while similarly treated Champion Dwarf produced none. It is the observation of inflorescence on these cultivars (which are rated as very low seedhead producers, (see Beard, J.B., *Turf Grass: Science and Culture* (Prentice-Hall, Inc.)), while seeing no inflorescence on the Champion Dwarf cultivar growing adjacent to them that has been so striking.

Cynodon species are indeterminate, or day-neutral, seedhead producers. In Bay City, Tex., the Bermudagrasses can be observed producing seedheads during the transition from spring to summer, and again from summer to fall. Again, the Champion Dwarf cultivar has produced no seedheads during these periods, or any other time.

In addition to the observations made throughout the course of multiple growing seasons, the Champion Dwarf cultivar has failed to produce any seedheads even in situations specifically intended to induce inflorescence. Specifically, the Champion Dwarf cultivar was provided an excessive amount of fertilizer and kept well watered to produce very lush growth, and then the cultivar was abruptly denied water in the heat of summer. This caused the other three cultivars (Tifway, Tifgreen, and Tifdwarf) to produce numerous seedheads, but the Champion Dwarf cultivar produced none. In addition to the side-by-side comparisons in Bay City, the grass has been grown for locations with dissimilar climates, such as Palm Desert, Calif., and Auburn, Ala. No inflorescence development has been observed in the Champion Dwarf in these locations either.

Terminal Height

Figure 14:
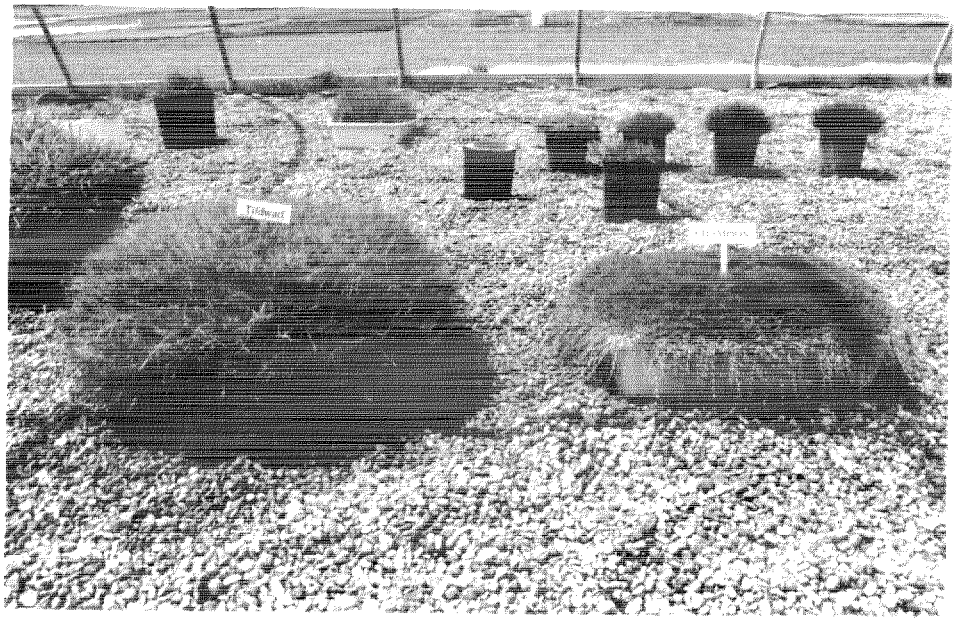
FIG. 14 is a photograph comparing the terminal height reached by Tifdwarf and Champion Dwarf after five months of growth.

The unmowed shoot growth height of Champion Dwarf was observed to be approximately 2". This is significantly lower than that of the other cultivars. For example, FIG. 14 shows the noticeably lower terminal height of Champion Dwarf versus Tifdwarf.

Detailed Characteristics

A detailed description of the new and distinct genotype of hybrid Bermudagrass named Champion Dwarf includes:

1. a unique slow vertical leaf extension rate;

2. a very low growth habit via vigorous lateral stem growth by stolons and rhizomes;

3. a high shoot density that produces a uniform, high-quality turf surface;

4. an absence of influorescence or seedhead formation under turf culture;

5. the leaves are folded in the bud shoot;

6. the leaf blades are flattened to v-shaped in cross-section, keeled, and gradually tapering to an acute point;

7. the leaf width is in the order of 1 mm under very close mowing;

8. the ligule at the junction of the leaf blade and leaf sheath is a fringe-of-hairs;

9. there is no auricle present;

10. the collar on the opposite side from the ligule is a continuous, narrow band;

11. the internode length of stolons is in the order of 12 to 13 mm;

12. the lateral stems, both stolons and rhizomes, branch profusely at the nodes;

13. each node-cluster produces three leaves;

14. the roots originate from nodes and are fine, fibrous, and dense; and 15. the unmowed shoot growth height is on the order of 2 inches (50 mm).

What is claimed is:

1. A new and distinct Bermudagrass plant having 2n=27 chromosomes, substantially as herein shown and described, distinguished by a minimum vertical leaf extension rate in conjunction with rapid, dense lateral stem growth.

* * * * *

UNITED STATES PATENT AND TRADEMARK OFFICE

CERTIFICATE OF CORRECTION

PATENT NO. : Plant 9,888

DATED : 05/06/97

INVENTOR(S) : Brown, et al.

It is certified that error appears in the above-identified patent and that said Letters Patent is hereby corrected as shown below:

In column 1, line 8, please delete "of" and insert in its place —or—.

In column 2, line 2, please delete "unslightly" and insert in its place —unsightly—.

In column 2, line 10, please insert a blank space between "1/8" and "of".

In column 3:

line 2 of SUMMARY OF THE INVENTION, please insert a space between "X" and "Cynodon";

line 12 of SUMMARY OF THE INVENTION, please insert a space between "x" and "Cynodon".

In column 4, line 2, please delete "subject" and insert in its place —subjected—.

In column 4:

line 5 of DETAILED DESCRIPTION OF THE PREFERRED EMBODIMENT, please insert a blank space between "x" and "Cynodon";

line 16 of DETAILED DESCRIPTION OF THE PREFERRED EMOBIDMENT, please insert a blank space between "x" and "Cynodon";

line 2 of Taxonomy—DNA Classification, please insert a blank space between "x" and "Cynodon";

line 7 of Morphological Characterization, please delete "speed" and insert in its place —spread—; and line 8 of Morphological Characterization, please insert —very— before "rapidly".

In column 7, line 4 of Formation of Mat, insert —grass— after "gives".

UNITED STATES PATENT AND TRADEMARK OFFICE

CERTIFICATE OF CORRECTION

PATENT NO. : Plant 9,888
DATED : May 6, 1997
INVENTOR(S) : Brown, et. al.

It is certified that error appears in the above-indentified patent and that said Letters Patent is hereby corrected as shown below:

In column 9, last paragraph under Table 8, please delete "Draft" and insert in its place --Dwarf--.

Signed and Sealed this

Twenty-sixth Day of August, 1997

*Attest:*

Bruce Lehman

BRUCE LEHMAN

*Attesting Officer*

*Commissioner of Patents and Trademarks*